US005118494A

United States Patent [19]

Schultz et al.

[11] Patent Number: 5,118,494
[45] Date of Patent: Jun. 2, 1992

[54] USE OF SOLUBLE FLUOROSURFACTANTS FOR THE PREPARATION OF METERED-DOSE AEROSOL FORMULATIONS

[75] Inventors: Robert K. Schultz, Shoreview; Stephen N. Quessy, St. Paul, both of Minn.

[73] Assignee: Minnesota Mining and Manufacturing Company, St. Paul, Minn.

[21] Appl. No.: 668,597

[22] Filed: Mar. 13, 1991

Related U.S. Application Data

[63] Continuation-in-part of Ser. No. 498,333, Mar. 23, 1990.

[51] Int. Cl.[5] .................... A61K 9/12

[52] U.S. Cl. .................... 424/45; 514/456; 514/455; 514/291; 526/209; 564/412

[58] Field of Search .................... 514/456, 291, 455; 424/45; 526/209; 564/412

[56] References Cited

U.S. PATENT DOCUMENTS

| | | | |
|---|---|---|---|
| 2,868,691 | 1/1959 | Porush et al. | 167/54 |
| 3,104,844 | 12/1961 | Thiel et al. | 167/82 |
| 3,250,808 | 5/1966 | Moore et al. | 260/535 |
| 4,174,295 | 11/1979 | Gargigia et al. | 252/305 |
| 4,352,789 | 10/1982 | Thiel | 424/46 |
| 4,405,598 | 9/1983 | Brown | 514/456 |
| 4,621,116 | 11/1986 | Morgan | 526/209 |
| 4,810,488 | 3/1989 | Jinks | 424/45 |
| 4,889,656 | 12/1989 | Flynn et al. | |
| 4,929,317 | 5/1990 | Nishimura | 564/412 |

FOREIGN PATENT DOCUMENTS

| | | |
|---|---|---|
| 0372777 | 11/1989 | European Pat. Off. . |
| 0379793 | 11/1989 | European Pat. Off. . |
| 0384371 | 8/1990 | European Pat. Off. . |

OTHER PUBLICATIONS

Research Disclosure, vol. 162, 1977 p. 70 (#16265).

*Primary Examiner*—Thurman K. Page
*Assistant Examiner*—William E. Benston
*Attorney, Agent, or Firm*—Gary L. Griswold; Walter N. Kirn; Douglas E. Reedich

[57] ABSTRACT

Pharmaceutical suspension aerosol formulations using one or more perfluorinated carboxylic acids or esters thereof as surface-active dispersing agents and 1,1,1,2-tetra-fluorethane or 1,1,1,2,3,3,3-heptafluoropropane as the propellant are described.

15 Claims, No Drawings

USE OF SOLUBLE FLUOROSURFACTANTS FOR THE PREPARATION OF METERED-DOSE AEROSOL FORMULATIONS

This application is a continuation-in-part of U.S. application No. 07/498,333. filed on Mar. 23, 1990, incorporated herein by reference.

TECHNICAL FIELD OF THE INVENTION

This invention relates to suspension aerosol formulations suitable for the administration of medicaments. More particularly, it relates to pharmaceutical suspension aerosol formulations using 1,1,1,2-tetrafluoroethane or 1,1,1,2,3,3,3-heptafluoropropane as the propellant.

BACKGROUND OF THE INVENTION

Pharmaceutical suspension aerosol formulations currently use a mixture of liquid chlorofluorocarbons as the propellant. Fluorotrichloromethane, dichlorodifluoromethane and dichlorotetrafluoroethane are the most commonly used propellants in aerosol formulations for administration by inhalation.

Chlorofluorocarbons have been implicated in the destruction of the ozone layer and their production is being phased out. Hydrofluorocarbon 134a (HFC-134a, 1,1,1,2-tetrafluoroethane) and hydrofluorocarbon 227 (HFC-227, 1,1,1,2,3,3,3-heptafluoropropane) are viewed as being more ozone friendly than many chlorofluorocarbon propellants; furthermore, they have low toxicity and vapor pressures suitable for use in aerosols.

U.S. Pat. No. 4,352,789 discloses a self-propelling, powder dispensing aerosol composition comprising between about 0.001 and 20 percent by weight of a finely-divided solid material coated with a dry coating of a perfluorinated surface-active dispersing agent of a particular type which constitutes between about 0.1 to 20 percent by weight of the coated solid and a halogenated propellant. The solid material can be a medicament. The use of 1,1,1,2-tetrafluoroethane or 1,1,1,2,3,3,3-heptafluoropropane as a propellant is not specifically disclosed. Perfluorinated carboxylic acid surfactants are not disclosed.

SUMMARY OF THE INVENTION

This invention provides suspension aerosol formulations comprising an effective amount of a powdered medicament, between about 0.001 and 0.6 percent by weight of a perfluorinated surface-active dispersing agent and a propellant comprising a hydrofluorocarbon selected from the group consisting of 1,1,1,2-tetrafluoroethane and 1,1,1,2,3,3,3-heptafluoropropane, and a mixture thereof.

The perfluorinated surface-active dispersing agent is a perfluorinated carboxylic acid or ester having the general formula

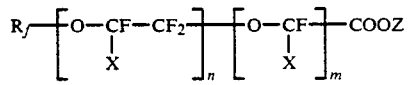

wherein $R_f$ is selected from the group consisting of perfluorinated straight chain, branched chain, or cyclic alkyl or combinations thereof containing three to about ten carbon atoms, wherein cyclic alkyl optionally contains one or more catenary oxygen or nitrogen atoms;

each X is independently selected from the group consisting of fluoro and straight chain or branched chain perfluoroalkyl of one to about four carbon atoms;

n and m are independently integers from zero to three with the proviso that the sum of n and m is less than or equal to four; and Z is selected from the group consisting of hydrogen and straight or branched chain alkyl containing one to about four carbon atoms, the formulation exhibiting substantially no crystallization of said medicament over a prolonged period, being substantially readily redispersible, and upon redispersion not flocculating so quickly as to prevent reproducible dosing of the medicament.

The pharmaceutical suspension aerosol formulations of the invention are suitable, for example, for dermal, pulmonary, or mucosal (e.g., buccal or nasal) administration.

DETAILED DESCRIPTION OF THE INVENTION

The term "suspension aerosol" means that the medicament is in powder form and is substantially insoluble in the propellant.

By "prolonged period" as used herein in the context of crystallization is meant at least about four (4) months.

The medicament is micronized, that is, over 90 percent of the particles have a diameter of less than about 10 microns.

The medicament is generally present in an amount effective to bring about the intended therapeutic effect of the medicament. The amount of medicament, however, depends on the potency of the particular medicament being formulated. Generally, the medicament constitutes from about 0.01 to 5 percent by weight of the total weight of the formulation, preferably about 0.01 to about 2 percent by weight of the total weight of the formulation.

Medicaments for delivery by inhalation include, for example, antiallergics, analgesics, bronchodilators, antihistamines, antitussives, anginal preparations, antibiotics, antiinflammatories, hormones, peptides, steroids, enzymes, sulfonamides, or a combination of these.

Examples of medicaments falling within the above therapeutic classes are: isoproterenol hydrochloride or sulfate, phenylephrine bitartrate or hydrochloride, pirbuterol acetate or hydrochloride, disodium cromoglycate, phenylpropanolamine, glucagon, adrenochrome, trypsin, epinephrine bitartrate, ephedrine, narcosine, codeine, atropine, heparin, morphine, albuterol, albuterol sulfate, triamcinolone acetonide, beclomethasone dipropionate, flunisolide, formoterol, salmeterol, colchicine, neomycin, streptomycin, penicillin, tetracycline, chlorotetracycline, hydroxytetracycline, cortisone, hydrocortisone, prednisolone, and insulin.

Preferred medicaments in the practice of this invention include pirbuterol acetate, pirbuterol hydrochloride, disodium cromoglycate, albuterol sulfate, beclomethasone dipropionate, and triamcinolone acetonide.

Perfluorinated surface-active dispersing agents useful in the invention are perfluorinated carboxylic acids or mixture of such acids that are soluble in 1,1,1,2-tetrafluoroethane, 1,1,1,2,3,3,3-heptafluoropropane, or a mixture thereof.

Suitable perfluorinated carboxylic acids are those having the general formula:

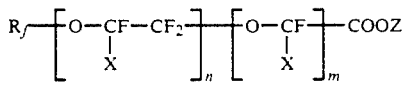

wherein $R_f$ is selected from the group consisting of perfluorinated straight chain, branched chain, or cyclic alkyl or combinations thereof containing three to about ten carbon atoms, wherein cyclic alkyl optionally contains one or more catenary oxygen or nitrogen atoms;

each X is independently selected from the group consisting of fluoro and straight chain or branched chain perfluoroalkyl of one to about four carbon atoms;

n and m are independently integers from zero to three with the proviso that the sum of n and m is less than or equal to four; and Z is selected from the group consisting of hydrogen and straight or branched chain alkyl containing one to about four carbon atoms.

When m and n are zero, the dispersing agent is perfluoro straight chain, branched chain, cyclic, or a combination thereof, alkanoic acid or ester. Perfluoroalkanoic acids are known and disclosed, e.g., in "Aliphatic Fluorine Compounds", American Chemical Society Monograph Series, Reinhold Publishing Corporation (1958), Chapter VII. Perfluoroalkanoic acid esters are known and disclosed, e.g., in Chapter IX of the same publication.

When either or both of m and n are non-zero, the dispersing agent is an acid- or ester-functional perfluoro mono-, di-, or polyether. Such perfluoroethers are known and disclosed, e.g., in U.S. Pat. Nos. 3,250,808 (Moore et al.) and 4,898,656 (Flynn et al.), incorporated herein by reference.

Particularly preferred perfluorinated carboxylic acids include perfluorobutanoic acid, perfluorooctanoic acid, and perfluorocyclohexylacetic acid.

The perfluorinated surface-active dispersing agent preferably has a solubility of at least 0.1 percent by weight, more preferably at least 0.3 percent by weight and most preferably at least 0.8 percent by weight in the propellant.

The perfluorinated surface-active dispersing agent constitutes from about 0.001 to about 0.6 percent by weight, preferably about 0.005 to about 0.5 percent by weight, of the aerosol formulation. The particular preferred amount depends on the particular medicament being formulated and on the particular surface-active dispersing agent being used. It is preferred that the amount of agent used be approximately the minimum needed to provide a suitable suspension.

The hydrofluorocarbon or mixture thereof is preferably the only propellant present in the formulations of the invention. However, one or more other propellants such as propellant 142b (1-chloro-1,1-difluoroethane) can also be present.

The suspension aerosol formulations of the invention can be prepared by first preparing a solution of the perfluorinated surface-active dispersing agent in the propellant and then suspending the medicament in the solution In order to prepare a formulation, the perfluorinated surface-active dispersing agent is placed in an aerosol vial, a continuous valve is crimped onto the vial and the vial is pressure filled with the propellant. The vial is shaken on an automatic shaker until all of the dispersing agent is in solution. The micronized medicament is then placed in a separate aerosol vial, a continuous valve is crimped onto the vial and the vial is pressure filled with the previously prepared solution. The medicament is then dispersed in the solution by mixing or homogenizing. If the medicament being formulated is moisture sensitive, these steps should be performed in a dehumidified atmosphere using only dry materials and equipment.

The following examples are provided to illustrate the invention but should not be construed as limiting the invention.

In the following examples the quality of the aerosol suspension is rated on a scale of 1 to 5 with 1 indicating a "poor" suspension and 5 indicating an "excellent" suspension. A poor suspension is characterized by one or more of the following: it has a rapid rate of settling or separation, it is difficult to redisperse after settling or separation, it forms large flocs quickly, and it exhibits crystal formation. In contrast, an excellent suspension is slow to settle or separate, is easily redispersed, has minimal flocculation, and exhibits no crystallization. Substantially no crystal formation, relative ease of redispersion, and absence of rapid flocculation after redispersion are important properties in order to provide reproducible dosing of the medicament. Absence of substantial crystal formation provides for maximization of the fraction of the dose deliverable to the target area of the lung. Ease of redispersion permits dosing of a uniform suspension. Finally, rapid flocculation results in a large variation in the dose delivered from the aerosol canister. Suspensions exhibiting a rating of 1 or 2 are not considered desirable in terms of an overall balance of properties of degree of crystallization, ease of redispersibility, and nature of any flocculation, whereas ones exhibiting a rating of 3, 4 or 5 are considered desirable and fall within the scope of this invention.

Except as otherwise indicated the propellant in the Examples below is 1,1,1,2-tetrafluoroethane (HFC-134a).

EXAMPLE 1

A 78.7 mg portion of perfluorooctanoic acid ("FC-26" from 3M) was placed in a 4 ounce vial, the vial was sealed with a continuous valve then pressure filled with 149.5 g of 1,1,1,2-tetrafluoroethane. The vial was then shaken on an automatic shaker for 15 minutes. The resulting stock solution contained 0.05% by weight of perfluorooctanoic acid. A 100 mg portion of micronized pirbuterol hydrochloride was placed in a 15 cc vial along with 5 ml of glass beads, the vial was sealed with a continuous valve then pressure filled with 20 g of the previously prepared stock solution. The vial was shaken on an automatic shaker for 10 minutes then placed on a WIG-L-BUGυ grinder/mixer for 30 seconds. The resulting suspension contained 0.5% by weight of pirbuterol hydrochloride and had a quality rating of 5 (excellent).

EXAMPLES 2-10

Using the general method of Example 1, a series of suspension aerosol formulations containing 0.5 percent by weight based on the total weight of the formulation of micronized pirbuterol hydrochloride was prepared. Table 1 shows the amount (percent by weight based on the total weight of the formulation) and identity of the surface-active dispersing agent used and the suspension quality rating.

TABLE 1

| Example | Surface-Active Dispersing Agent | | Rating |
|---|---|---|---|
| 2 | 0.002% | perfluorooctanoic acid | 1 |
| 3 | 0.006% | perfluorooctanoic acid | 4 |
| 4 | 0.01% | perfluorooctanoic acid | 4 |
| 5 | 0.3% | perfluorooctanoic acid | 5 |
| 6 | 0.006% | perfluorobutanoic acid | 5 |
| 7 | 0.012% | perfluorobutanoic acid | 5 |
| 8 | 0.059% | perfluorobutanoic acid | 5 |
| 9 | 0.310% | perfluorobutanoic acid | 5 |
| 10 | 0.507% | perfluorobutanoic acid | 5 |

EXAMPLES 11-20

Using the general method of Example 1, a series of suspension aerosol formulations containing 0.5 percent by weight based on the total weight of the formulation of micronized pirbuterol acetate was prepared. Table 2 shows the amount (percent by weight based on the total weight of the formulation) and identity of the surface-active dispersing agent used and the suspension quality rating.

TABLE 2

| Example | Surface-Active Dispersing Agent | | Rating |
|---|---|---|---|
| 11 | 0.002% | perfluorooctanoic acid | 1 |
| 12 | 0.006% | perfluorooctanoic acid | 2 |
| 13 | 0.01% | perfluorooctanoic acid | 2 |
| 14 | 0.05% | perfluorooctanoic acid | 3 |
| 15 | 0.3% | perfluorooctanoic acid | 3 |
| 16 | 0.006% | perfluorobutanoic acid | 2 |
| 17 | 0.012% | perfluorobutanoic acid | 2 |
| 18 | 0.059% | perfluorobutanoic acid | 2 |
| 19 | 0.310% | perfluorobutanoic acid | 2 |
| 20 | 0.507% | perfluorobutanoic acid | 2 |

EXAMPLES 21-29

Using the general method of Example 1, a series of suspension aerosol formulations containing 0.5 percent by weight based on the total weight of the formulation of micronized albuterol sulfate was prepared. Table 3 shows the amount (percent by weight based on the total weight of the formulation) and identity of the surface-active dispersing agent used and the suspension quality rating.

TABLE 3

| Example | Surface-Active Dispersing Agent | | Rating |
|---|---|---|---|
| 21 | 0.002% | perfluorooctanoic acid | 1 |
| 22 | 0.006% | perfluorooctanoic acid | 1 |
| 23 | 0.01% | perfluorooctanoic acid | 1 |
| 24 | 0.05% | perfluorooctanoic acid | 1 |
| 25 | 0.3% | perfluorooctanoic acid | 1 |
| 26 | 0.006% | perfluorobutanoic acid | 1 |
| 27 | 0.012% | perfluorobutanoic acid | 1 |
| 28 | 0.310% | perfluorobutanoic acid | 1 |
| 29 | 0.507% | perfluorobutanoic acid | 1 |

EXAMPLES 30-39

Using the general method of Example 1, a series of suspension aerosol formulations containing 1.5 percent by weight based on the total weight of the formulation of micronized disodium cromoglycate was prepared. Table 4 shows the amount (percent by weight based on the total weight of the formulation) and identity of the surface-active dispersing agent used and the suspension quality rating.

TABLE 4

| Example | Surface-Active Dispersing Agent | | Rating |
|---|---|---|---|
| 30 | 0.002% | perfluorooctanoic acid | 3 |
| 31 | 0.006% | perfluorooctanoic acid | 4 |
| 32 | 0.01% | perfluorooctanoic acid | 3 |
| 33 | 0.05% | perfluorooctanoic acid | 3 |
| 34 | 0.3% | perfluorooctanoic acid | 3 |
| 35 | 0.006% | perfluorobutanoic acid | 3 |
| 36 | 0.012% | perfluorobutanoic acid | 3 |
| 37 | 0.059% | perfluorobutanoic acid | 4 |
| 38 | 0.310% | perfluorobutanoic acid | 2 |
| 39 | 0.507% | perfluorobutanoic acid | 2 |

TABLE 4

| Example | Surface-Active Dispersing Agent | | Rating |
|---|---|---|---|
| 30 | 0.002% | perfluorooctanoic acid | 3 |
| 31 | 0.006% | perfluorooctanoic acid | 4 |
| 32 | 0.01% | perfluorooctanoic acid | 3 |
| 33 | 0.05% | perfluorooctanoic acid | 3 |
| 34 | 0.3% | perfluorooctanoic acid | 3 |
| 35 | 0.006% | perfluorobutanoic acid | 3 |
| 36 | 0.012% | perfluorobutanoic acid | 3 |
| 37 | 0.059% | perfluorobutanoic acid | 4 |
| 38 | 0.310% | perfluorobutanoic acid | 2 |
| 39 | 0.507% | perfluorobutanoic acid | 2 |

A preferred disodium cromoglycate formulation is the same as Example 31 above except the drug concentration is 0.5 percent by weight drug. This formulation had a suspension quality rating of 5.

EXAMPLES 40-49

Using the general method of Example 1, a series of suspension aerosol formulations containing 0.5 percent by weight based on the total weight of the formulation of micronized epinephrine bitartrate was prepared. Table 5 shows the amount (percent by weight based on the total weight of the formulation) and identity of the surface-active dispersing agent used and the suspension quality rating.

TABLE 5

| Example | Surface-Active Dispersing Agent | | Rating |
|---|---|---|---|
| 40 | 0.002% | perfluorooctanoic acid | 2 |
| 41 | 0.006% | perfluorooctanoic acid | 2 |
| 42 | 0.01% | perfluorooctanoic acid | 2 |
| 43 | 0.05% | perfluorooctanoic acid | 2 |
| 44 | 0.3% | perfluorooctanoic acid | 2 |
| 45 | 0.006% | perfluorobutanoic acid | 2 |
| 46 | 0.012% | perfluorobutanoic acid | 2 |
| 47 | 0.059% | perfluorobutanoic acid | 2 |
| 48 | 0.310% | perfluorobutanoic acid | 2 |
| 49 | 0.507% | perfluorobutanoic acid | 2 |

EXAMPLES 50-62

Using the general method of Example 1, a series of suspension aerosol formulations containing 0.3 percent by weight based on the total weight of the formulation of micronized triamcinolone acetonide was prepared. Table 6 shows the amount (percent by weight based on the total weight of the formulation) and identity of the surface-active dispersing agent used and the suspension quality rating.

TABLE 6

| Example | Surface-Active Dispersing Agent | | Rating |
|---|---|---|---|
| 50 | 0.05% | perfluorooctanoic acid | 4 |
| 51 | 0.05% | isopropyl perfluoro-cyclohexanecarboxylate | 2 |
| 52 | 0.05% | perfluoro-2-ethoxy- | 3 |

TABLE 6-continued

| Example | Surface-Active Dispersing Agent | | Rating |
|---|---|---|---|
| | | ethoxyacetic acid | |
| 53 | 0.05% | methyl perfluoro-2-ethoxyethoxyacetate | 3 |
| 54 | 0.05% | perfluoro-2-butoxypropionic acid | 2 |
| 55 | 0.005% | perfluoro-2-butoxypropionic acid | 2 |
| 56 | 0.05% | perfluoro-3-butoxypropionic acid | 3 |
| 57 | 0.05% | methyl perfluoro-3-butoxypropionate | 3 |
| 58 | 0.05% | isopropyl perfluoro-2-butoxyethoxy acetate | 3 |
| 59 | 0.05% | perfluoro-2-hexyloxyethoxyacetic acid | 3 |
| 60 | 0.005% | perfluoro-2-hexyloxyethoxyacetic acid | 4 |
| 61 | 0.05% | perfluoro-3-octyloxypropionic acid | 3 |
| 62 | 0.005% | perfluoro-3-octyloxypropionic acid | 3 |

EXAMPLES 63–72

Using the general method of Example 1, a series of suspension aerosol formulations containing 0.5 percent by weight based on the total weight of the formulation of micronized pirbuterol acetate was prepared. Table 7 shows the amount (percent by weight based on the total weight of the formulation) and identity of the surface-active dispersing agent used and the suspension quality rating.

TABLE 7

| Example | Surface-Active Dispersing Agent | | Rating |
|---|---|---|---|
| 63 | 0.05% | isopropyl perfluorocyclohexanecarboxylate | 2 |
| 64 | 0.05% | perfluorocyclohexylacetic acid | 4 |
| 65 | 0.05% | perfluoro-2-ethoxyethoxyacetic acid | 5 |
| 66 | 0.05% | methyl perfluoro-2-ethoxyethoxyacetate | 5 |
| 67 | 0.05% | perfluoro-2-butoxypropionic acid | 5 |
| 68 | 0.05% | perfluoro-3-butoxypropionic acid | 5 |
| 69 | 0.05% | methyl perfluoro-3-butoxypropionate | 4 |
| 70 | 0.05% | isopropyl perfluoro-2-butoxyethoxyacetate | 5 |
| 71 | 0.05% | perfluoro-2-hexyloxyethoxyacetic acid | 5 |
| 72 | 0.05% | perfluoro-3-octyloxypropionic acid | 5 |

EXAMPLES 73–76

Using the general method of Example 1, a series of suspension aerosol formulations containing 1.5 percent by weight based on the total weight of the formulation of micronized disodium cromoglycate was prepared. Table 8 shows the amount (percent by weight based on the total weight of the formulation) and identity of the surface-active dispersing agent used and the suspension quality rating.

TABLE 8

| Example | Surface-Active Dispersing Agent | | Rating |
|---|---|---|---|
| 73 | 0.05% | isopropyl perfluorocyclohexanecarboxylate | 2 |
| 74 | 0.05% | perfluoro-2-butoxypropionic acid | 5 |

TABLE 8-continued

| Example | Surface-Active Dispersing Agent | | Rating |
|---|---|---|---|
| 75 | 0.005% | perfluoro-2-butoxypropionic acid | 4 |
| 76 | 0.05% | isopropyl perfluoro-2-butoxyethoxy acetate | 5 |

EXAMPLES 77–78

Using the general method of Example 1, two suspension aerosol formulations containing 0.5 percent by weight based on the total weight of the formulation of micronized albuterol sulfate were prepared. Table 9 shows the amount (percent by weight based on the total weight of the formulation) and identity of the surface-active dispersing agent used and the suspension quality rating.

TABLE 9

| Example | Surface-Active Dispersing Agent | | Rating |
|---|---|---|---|
| 77 | 0.05% | perfluoro-2-butoxypropionic acid | 4 |
| 78 | 0.005% | perfluoro-2-butoxypropionic acid | 3 |

EXAMPLES 79–83

Using the general method of Example 1, a series of suspension aerosol formulations containing micronized beclomethasone dipropionate was prepared. Table 10 shows the amount (percent by weight based on the total weight of the formulation) and identity of the surface-active dispersing agent used and the suspension quality rating. In the suspensions of Examples 79–81 the medicament was present in an amount by weight of 0.1% and in those of Examples 82 and 83 it was present in an amount by weight of 0.3%.

TABLE 10

| Example | Surface-Active Dispersing Agent | | Rating |
|---|---|---|---|
| 79 | 0.05% | perfluorooctanoic acid | 3 |
| 80 | 0.05% | methyl perfluoro-2-ethoxyethoxyacetate | 4 |
| 81 | 0.05% | methyl perfluoro-3-butoxypropionate | 4 |
| 82 | 0.05% | perfluoro-2-butoxypropionic acid | 2 |
| 83 | 0.005% | perfluoro-2-butoxypropionic acid | 2 |

EXAMPLES 84–87

A 10.99 g portion of beclomethasone dipropionate and about 81.8 g of acetone were placed in a 4 ounce glass vial and warmed on a steam bath until a solution was obtained. The solution was divided evenly among four 4 ounce vials each containing approximately 100 mL of 1,1,1,2-tetrafluoroethane. The vials were placed in a refrigerator overnight. The resulting precipitate was collected by filtration then dried under vacuum to provide beclomethasone dipropionate-1,1,1,2-tetrafluoroethane clathrate. The clathrate was micronized using a fluid energy micronizer. Using the general method of Example 1, a series of suspension aerosol formulations containing 0.1% by weight based on the total weight of the formulation of the micronized clathrate was prepared. Table 11 shows the amount (percent by weight based on the total weight of the formulation) and identity of the surface-active dispersing agent used and the suspension quality rating.

TABLE 11

| Example | Surface-Active Dispersing Agent | | Rating |
|---------|------|------|--------|
| 84 | 0.05% | methyl perfluoro-3-butoxypropionate | 5 |
| 85 | 0.05% | perfluoro-3-butoxypropionic acid | 5 |
| 86 | 0.05% | perfluoro-2-ethoxyethoxyacetic acid | 4 |
| 87 | 0.05% | methyl perfluoro-2-ethoxyethoxyacetate | 5 |

EXAMPLES 88–91

A series of aerosol suspension formulations in which 1,1,1,2,3,3,3-heptafluoropropane (HFC-227) serves as the propellant was prepared using the general method of Example 1. Table 12 shows the amount (percent by weight based on the total weight of the formulation) and identity of the surface-active dispersing agent used and the suspension quality rating. The formulations of Examples 88 and 89 contained 0.5 percent by weight based on the total weight of the formulation of micronized pirbuteraol acetate. Those of Examples 90 and 91 contained 0.3 percent by weight of micronized triamcinolone acetonide.

TABLE 12

| Example | Surface-Active Dispersing Agent | | Rating |
|---------|------|------|--------|
| 88 | 0.05% | perfluorooctanoic acid | 4 |
| 89 | 0.05% | perfluoro-2-butoxypropionic acid | 4 |
| 90 | 0.05% | perfluorooctanoic acid | 3 |
| 91 | 0.05% | perfluoro-2-butoxypropionic acid | 3 |

What is claimed is:

1. A suspension aerosol formulation, comprising: a propellant comprising a hydrofluorocarbon selected from the group consisting of 1,1,1,2-tetrafluoroethane and 1,1,1,2,3,3,3-heptafluoropropane, and a mixture thereof; a therapeutically effective amount of a powdered medicament; and between about 0.001 and 0.6 percent by weight based on the total weight of said formulation of a surface-active dispersing agent of the formula $$R_f \left[ O-CF-CF_2 \atop X \right]_n \left[ O-CF \atop X \right]_m COOZ$$

wherein $R_f$ is selected from the group consisting of perfluorinated straight chain, branched chain, or cyclic alkyl or combinations thereof containing three to about ten carbon atoms, wherein cyclic alkyl optionally contains one or more catenary oxygen or nitrogen atoms;

each X is independently selected from the group consisting of fluoro and straight chain or branched chain perfluoroalkyl of one to about four carbon atoms, n and m are independently integers from zero to three with the proviso that the sum of n and m is less than or equal to four; and Z is selected from the group consisting of hydrogen and straight or branched chain alkyl containing one to about four carbon atoms, the formulation exhibiting substantially no crystallization of said medicament over a prolonged period, being substantially readily redispersible, and upon redispersion non flocculating so quickly as to prevent reproducible dosing of the medicament.

2. A suspension aerosol formulation according to claim 1 wherein said powdered medicament is present in an amount of from about 0.01 to 2 percent by weight based on the total weight of said formulation.

3. A suspension aerosol formulation according to claim 1 wherein said dispersing agent is present in an amount of from about 0.005 to 0.5 percent by weight based on the total weight of said formulation.

4. A suspension aerosol formulation according to claim 1 wherein said dispersing agent has a solubility of at least 0.3 percent by weight in the propellant.

5. A suspension aerosol formulation according to claim 4 wherein said agent has a solubility of at least 0.8 percent by weight in the propellant.

6. A suspension aerosol formulation according to claim 1 wherein m and n are zero.

7. A suspension aerosol formulation according to claim 6, wherein $R_f$ contains three to about seven carbon atoms.

8. A suspension aerosol formulation according to claim 1 wherein said surface-active dispersing agent is selected from the group consisting of perfluorobutanoic acid, perfluorooctanoic acid, perfluorocyclohexylacetic, acid, and $C_1$ through $C_4$ straight chain or branched chain alkyl esters thereof.

9. A suspension aerosol formulation according to claim 1 wherein said surface-active dispersing agent is selected from the group consisting of perfluoro-2-ethoxyethoxyacetic acid, perfluoro-2-butoxypropionic acid, perfluoro-3-butoxypropionic acid, perfluoro-2-butoxyethoxyacetic acid, perfluoro-2-hexyloxyethoxyacetic acid, and perfluoro-3-octyloxypropionic acid, and $C_1$ through $C_4$ straight chain or branched chain alkyl esters thereof.

10. A suspension aerosol formulation according to claim 1 wherein said medicament is selected from the group consisting of pirbuterol acetate, pirbuterol hydrochloride, disodium cromoglycate, albuterol sulfate, beclomethasone dipropionate, and triamcinolone acetonide.

11. A suspension aerosol formulation according to claim 1 comprising between about 0.1 to about 1.0 percent by weight based on the total weight of said formulation of pirbuterol hydrochloride having a substantially uniform particle size of less than about 10 microns in diameter, between about 0.005 and about 0.6 percent by weight based on the total weight of said formulation of perfluorobutanoic acid, and 1,1,1,2-tetrafluoroethane.

12. A suspension aerosol formulation according to claim 1 comprising between about 0.1 to about 1 percent by weight based on the total weight of said formulation of pirbuterol hydrochloride having a substantially uniform particle size of less than about 10 microns in diameter, between about 0.005 to about 0.4 percent by weight based on the total weight of said formulation of perfluorooctanoic acid, and 1,1,1,2-tetrafluoroethane.

13. A suspension aerosol formulation according to claim 1 comprising between about 0.1 to about 2 percent by weight based on the total weight of said formulation of disodium cromoglycate having substantially uniform particle size of less than about 10 microns in diameter, between about 0.005 to about 0.4 percent by weight based on the total weight of said formulation of perfluorooctanoic acid, and 1,1,1,2-tetrafluoroethane.

14. A suspension aerosol formulation according to claim 1 comprising 1,1,1,2-tetrafluoroethane as essentially the only propellant.

15. A suspension aerosol formulation according to claim 1 comprising 1,1,1,2,3,3,3-heptafluoropropane as essentially the only propellant.

* * * * *